(12) United States Patent
Awad et al.

(10) Patent No.: US 9,713,624 B1
(45) Date of Patent: Jul. 25, 2017

(54) SYNTHESIS OF RUTIN NANOTUBES (71) Applicant: KING SAUD UNIVERSITY, Riyadh (SA)

(72) Inventors: Manal Ahmed Gasmelseed Awad, Riyadh (SA); Mohamed Mahmoud Hafez Ahmed, Riyadh (SA); Othman A. Al-Shabanah, Riyadh (SA); Zeinab Korany Mohamed Hassan, Cairo (EG)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/364,225

(22) Filed: Nov. 29, 2016

(51) Int. Cl.
| | |
|---|---|
| *A61K 9/51* | (2006.01) |
| *B82Y 30/00* | (2011.01) |
| *B82Y 40/00* | (2011.01) |
| *A61K 31/7048* | (2006.01) |
| *A61K 9/00* | (2006.01) |

(52) U.S. Cl.
CPC ........ *A61K 31/7048* (2013.01); *A61K 9/0092* (2013.01)

(58) Field of Classification Search
None
See application file for complete search history.

(56) References Cited

U.S. PATENT DOCUMENTS 8,017,147 B2   9/2011 Mazed et al.

FOREIGN PATENT DOCUMENTS

| CN | 104292281 | 1/2015 |
| JP | H04368331 | 12/1992 |

*Primary Examiner* — Robert A Wax
*Assistant Examiner* — Randeep Singh
(74) *Attorney, Agent, or Firm* — Richard C. Litman (57) ABSTRACT

The synthesis of rutin nanotubes includes the steps of providing rutin powder; mixing the rutin powder with a solvent mixture of methanol, dimethyl sulfoxide, and hydrochloric acid to prepare a rutin solution; adding the rutin solution to boiling water dropwise; maintaining the rutin solution and water under ultrasonic conditions at room temperature for about 20 minutes; continuously stirring the solution until rutin nanoparticles are formed; and isolating the rutin nanotubes by centrifugation. A method of controlling the metastatic activity of cancer cells includes administering an effective amount of rutin nanotubes and nanoparticles prepared as described above to a site of metastatic activity in a mammal.

9 Claims, 14 Drawing Sheets

SYNTHESIS OF RUTIN NANOTUBES

BACKGROUND OF THE INVENTION

1. Field of the Invention

The present invention relates generally to nanoparticle synthesis, and particularly to the synthesis of rutin nanotubes for anti-cancer therapy.

2. Description of the Related Art

Novel drug delivery systems can greatly improve the performance of drugs in terms of efficacy, solubility, and bioavailability. Particularly, a nanoparticle system is one of the novel drug delivery systems that is emerging as a highly promising technology in enhancing drug delivery. It has already been successfully used to improve the physicochemical profiles of drug compounds and increase their bioavailability.

Cervical cancer is the third most common cancer in women worldwide and the seventh overall. Human papillomavirus (HPV) is so strongly associated with cervical cancer that the incidence of this malignancy is deemed as a surrogate indicator of HPV infection in countries lacking epidemiological studies. The anti-metastatic treatment failure may be due to multidrug resistance to standard therapies, which can be either primary (preceding drug exposure) or acquired resistance (induced by treatment). Clinical trials for cancer therapies using matrix metalloproteinase (MMP) inhibitors have generally had unsuccessful results. Therefore, in an attempt to find compounds that could have anti-metastatic effect, especially via MMP suppression with no toxicity, it would be desirable to investigate the effect of rutin nanotubes on the metastatic activity of cervical cancer infected by HPV (Hela cells).

Thus, the synthesis of rutin nanotubes solving the aforementioned problems is desired.

SUMMARY OF THE INVENTION

The synthesis of rutin nanotubes includes providing rutin powder; mixing the rutin powder with a mixture of methanol, dimethyl sulfoxide and hydrochloric acid to prepare a rutin solution; and adding the rutin solution to boiling water dropwise; maintaining the rutin solution and water under ultrasonic conditions at room temperature for about twenty minutes; continuously stirring the solution until rutin nanoparticles or nanotubes are formed; and isolating the rutin nanoparticles or nanotubes by centrifugation.

A method of controlling the metastatic activity of cancer cells includes administering an effective amount of rutin nanoparticles or nanotubes prepared according to the present method to a site of metastatic activity in a mammal.

These and other features of the present invention will become readily apparent upon further review of the following specification and drawings.

BRIEF DESCRIPTION OF THE DRAWINGS

4E and 4F are photomicrographs of a cell culture treated with 20 μg of rutin nanotubes prepared according to the present method in a scratched wound healing assay at 0-hour and after 24 hours, respectively.

Similar reference characters denote corresponding features consistently throughout the attached drawings.

DETAILED DESCRIPTION OF THE PREFERRED EMBODIMENTS

The synthesis of rutin nanotubes includes providing rutin powder; mixing the rutin powder with a mixture of methanol, dimethyl sulfoxide and hydrochloric acid to prepare a rutin solution; adding the rutin solution to boiling water dropwise; maintaining the rutin solution and water under ultrasonic conditions at room temperature for about 20 minutes; continuously stirring the solution until rutin nanoparticles or nanotubes are formed; and isolating the rutin nanoparticles or nanotubes by filtration or centrifugation. The synthesis of rutin nanotubes can further include drying the rutin nanoparticles or nanotubes to obtain a yellow powder. The adding of the rutin solution is typically completed under about 10 minutes. The ultrasonic conditions include irradiation of ultrasonic waves at a frequency of about 30 to about 60 kHz at a power of about 100 watts. The rutin nanoparticles or nanotubes prepared by the present technique display a mean diameter in the range of from about 10 nm to about 300 nm, and can have spherical, spheroidal, elongated spherical, rod-shaped, and/or faceted shapes.

The rutin nanotubes prepared by this method can be used for controlling the metastatic activity of cancer cells by administering an effective amount of the rutin nanotubes to a site of metastatic activity in a mammal. The cancer cells can include cervical cancer cell line infected by human papilloma virus, but it is not limited thereto.

Rutin (3-rhamnoglucosyl-3,5,7,3,4-pentahydroxyflavone) relates to the flavonoid family and it is contained in citrus fruit, buckwheat leaves and flowers. Rutin is also known as vitamin P, has the empirical formula $C_{27}H_{30}O_{16}$, and has the structural formula shown below:

Rutin favorably influences the blood vessel walls, lowers the risk of cardiovascular diseases, possesses antioxidant properties and inhibits formation of free radicals in the organism.

As used herein, the term "Hela cell" is a cell type in an immortal cell line used in scientific research, and it is the oldest and most commonly used human cell line. The line was derived from cervical cancer cells taken from Henrietta Lacks, a cervical cancer patient who died of this disease. The term "metastasis" refers to the spread of a cancer or other disease from one organ or part of the body to another without being directly connected with it. Matrix metalloproteinases (MMPs), also known as matrixins, are calcium-dependent zinc-containing endopeptidases that are enzymes related to tissue healing/remodeling and cancer cell metastasis. As used herein, the term "Nanoparticle" or "Nanotube" refers to a particle having at least one dimension sized between 1 and 100 nanometers. The nanoparticles can include rutin nanoparticles and nanotubes. In some embodiments, the nanoparticles disclosed herein are from about 5 nm to about 500 nm in diameter, e.g., 100 to 200 nm. As used herein, the term "ultrasonication" refers to irradiation with ultrasonic (>20 kHz) waves. Ultrasonication may be performed using an ultrasonic bath or an ultrasonic probe.

The following examples will further illustrate the process of preparing the rutin nanotubes/nanoparticles and their anti-metastatic activity.

Example 1

Synthesis of Rutin Nanotubes

Figure 1A:
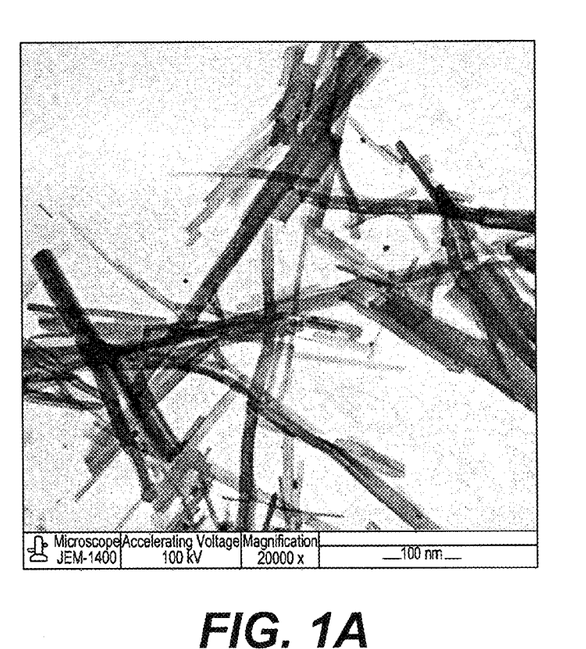
FIGS. 1A, 1B, 1C, and 1D are TEM micrographs of rutin nanotubes prepared by the present method at 20000×, 12000×, 12000×, and 80000× magnification, respectively.
Figure 1B:
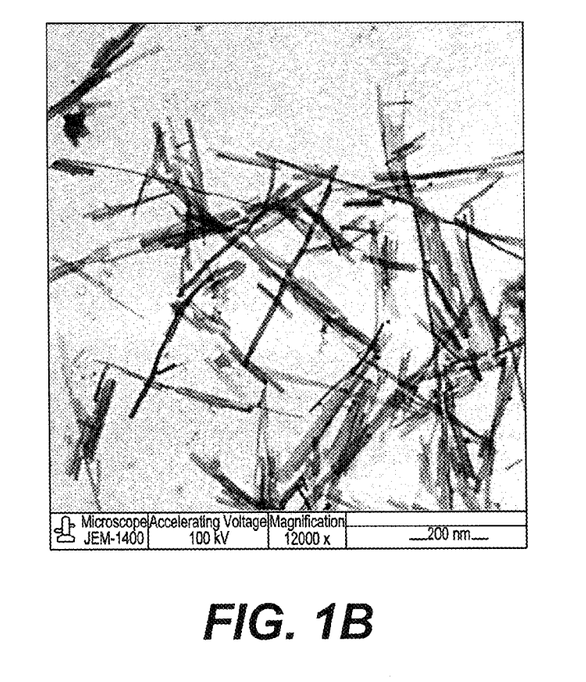
Figure 1C:
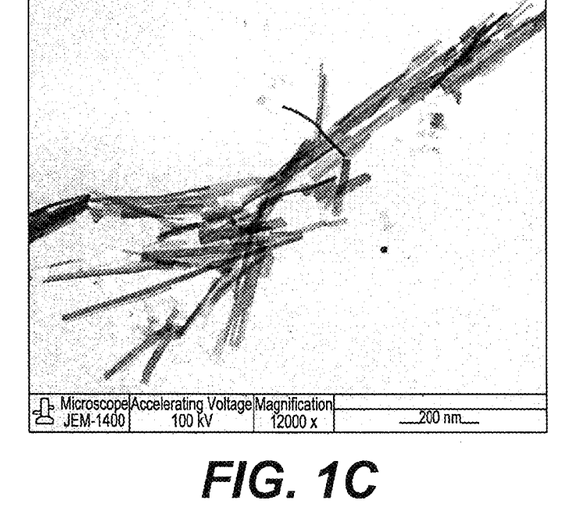
Figure 1D:
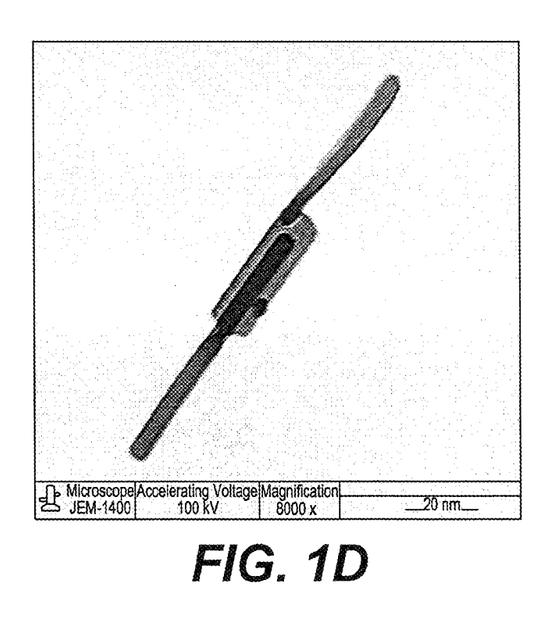
Figure 2:
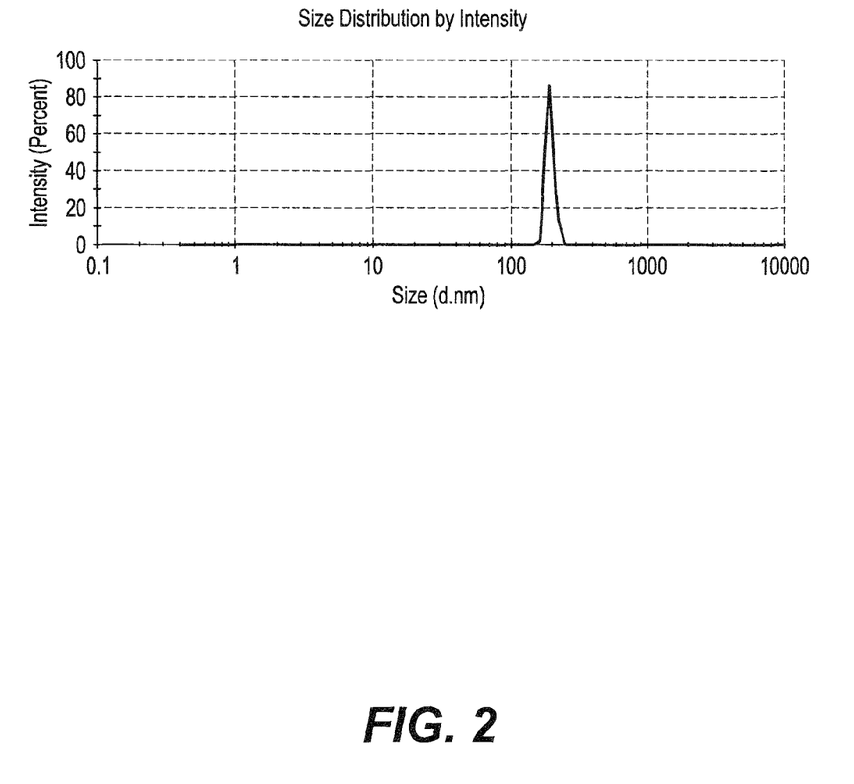
FIG. 2 is a graph showing the particle size distribution of rutin nanotubes prepared by the present method as measured by intensity.

About 100 mg of rutin powder (non-metal) was dissolved in a solvent mixture, which contained 10 ml methanol, 5 ml dimethyl sulfoxide (DMSO), and 1 ml of hydrochloric acid. Next, about 3 ml of the rutin solution was sprayed into about 30 ml of boiling water dropwise in about 10 minutes under ultrasonic conditions. After conducting ultrasonication for 20 minutes, the contents were stirred for about 15 minutes, then centrifuged and dried to obtain a yellow powder comprising rutin nanotubes (non-metal). FIGS. 1A-1D show the transmission electron microscopy (TEM) images of rutin nanotubes in different magnification scales. The nanotubes appear needle-like in structure. FIG. 2 shows the rutin nanotube particle size distribution, indicating that the average particle size of the resulting nanotubes is about 100-200 nm.

Example 2

Anti-Metastatic Assay of Rutin Nanotube on Hela Cells

Figure 3A:
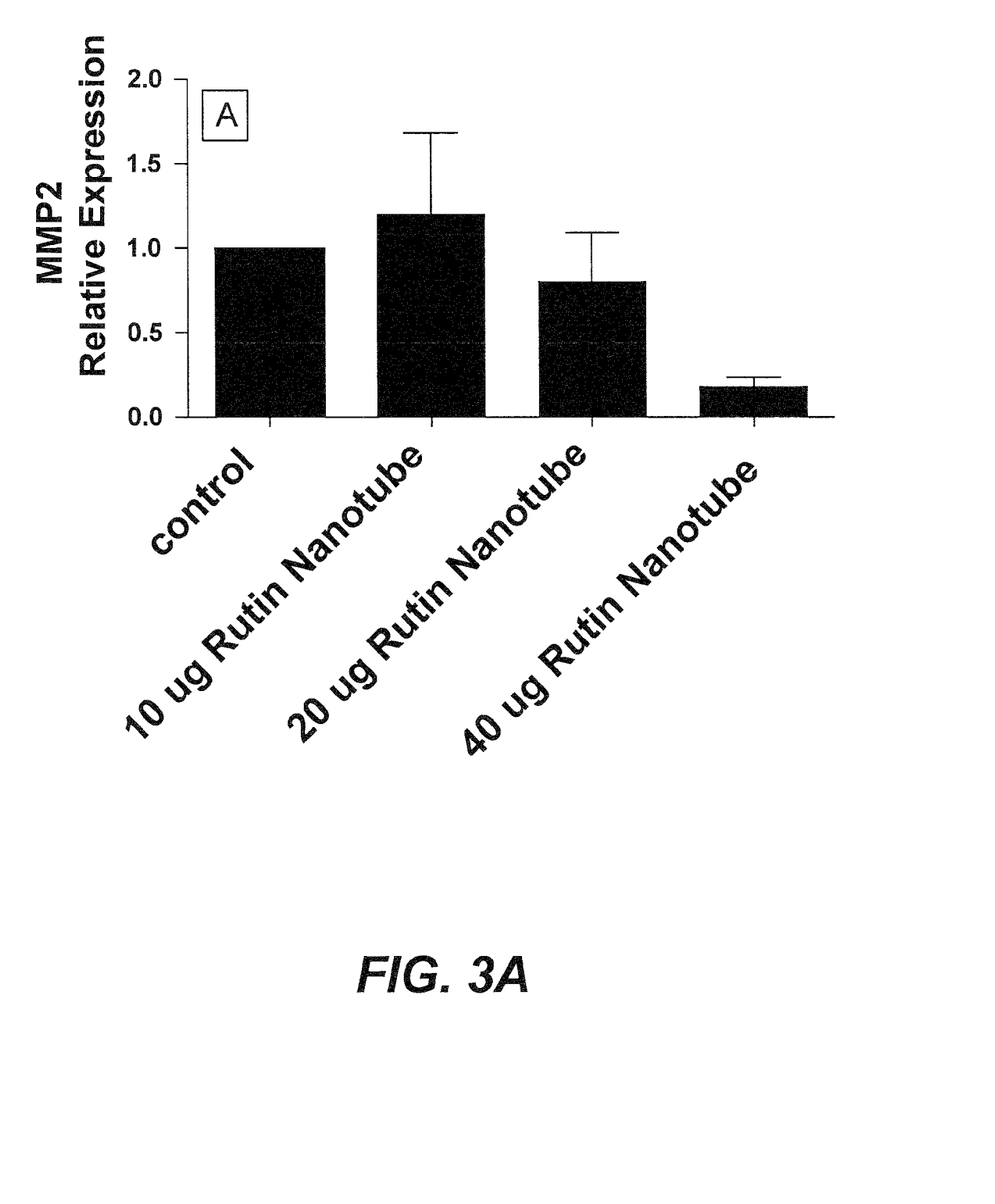
FIGS. 3A, 3B, and 3C are histograms showing real-time quantitative PCR assay results of the effect of the concentration of rutin nanotubes prepared according to the present method on the expression level of MMP2, MMP9, and TIMP3, respectively.
Figure 3B:
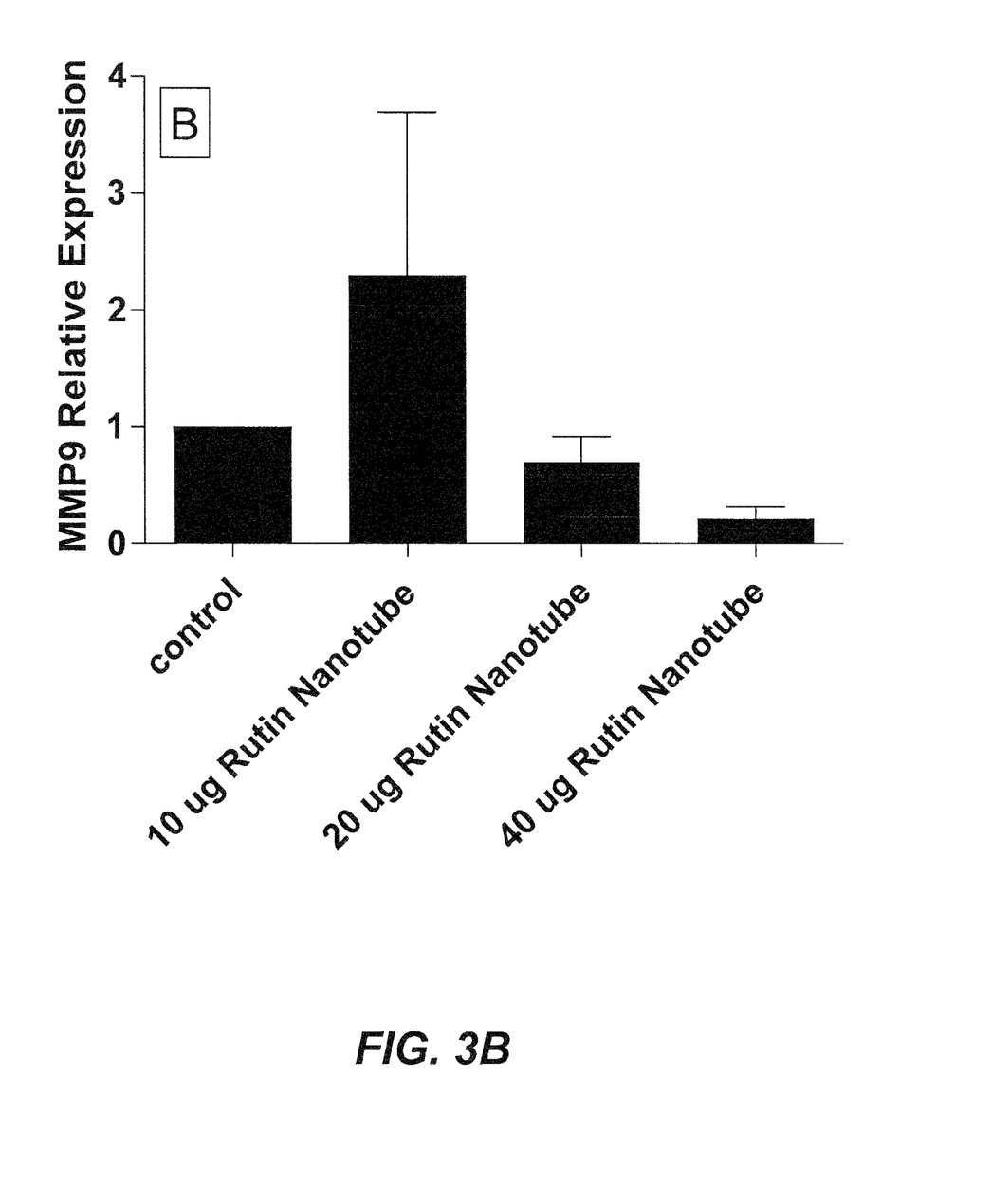
Figure 3C:
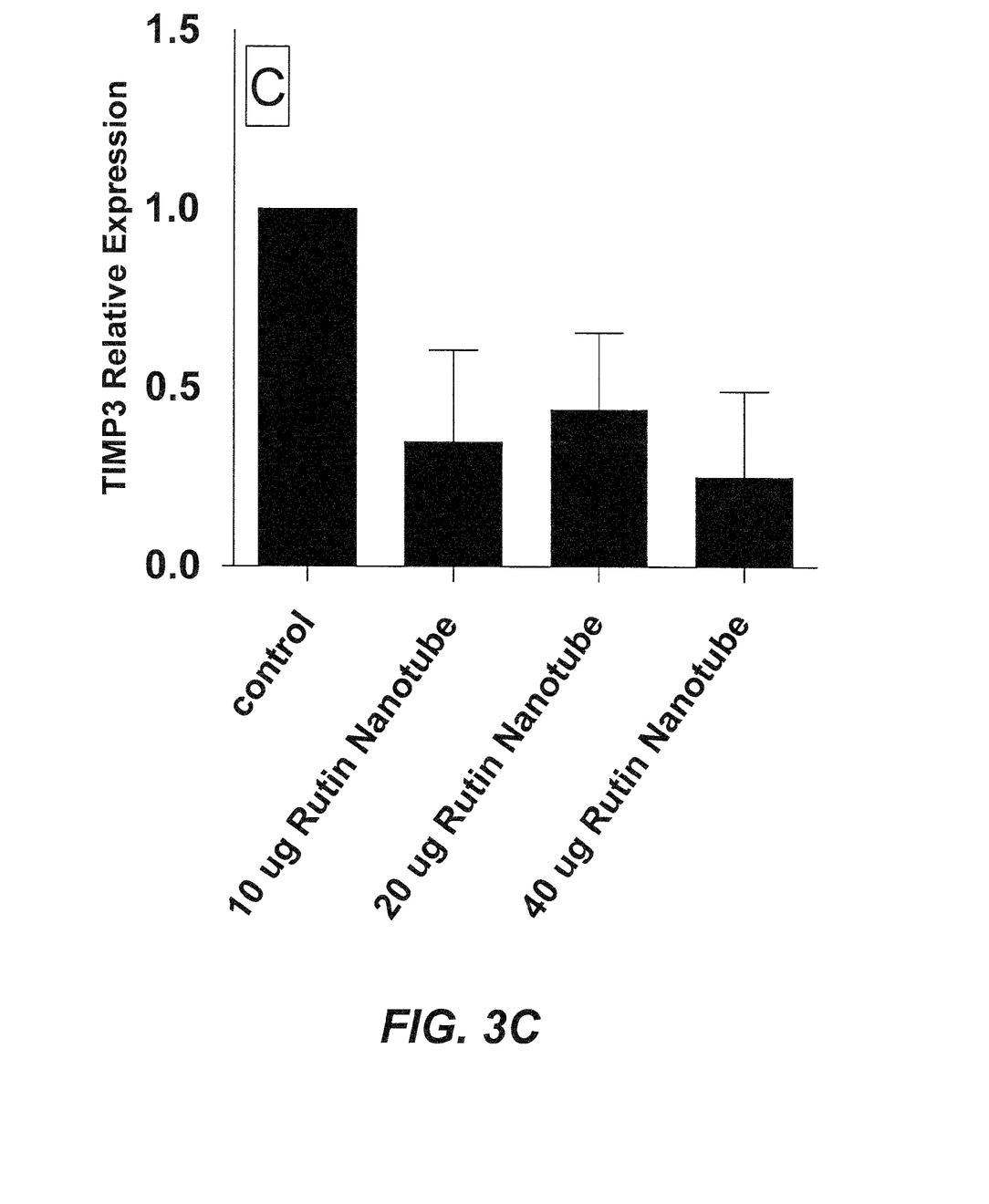
Figure 4A:
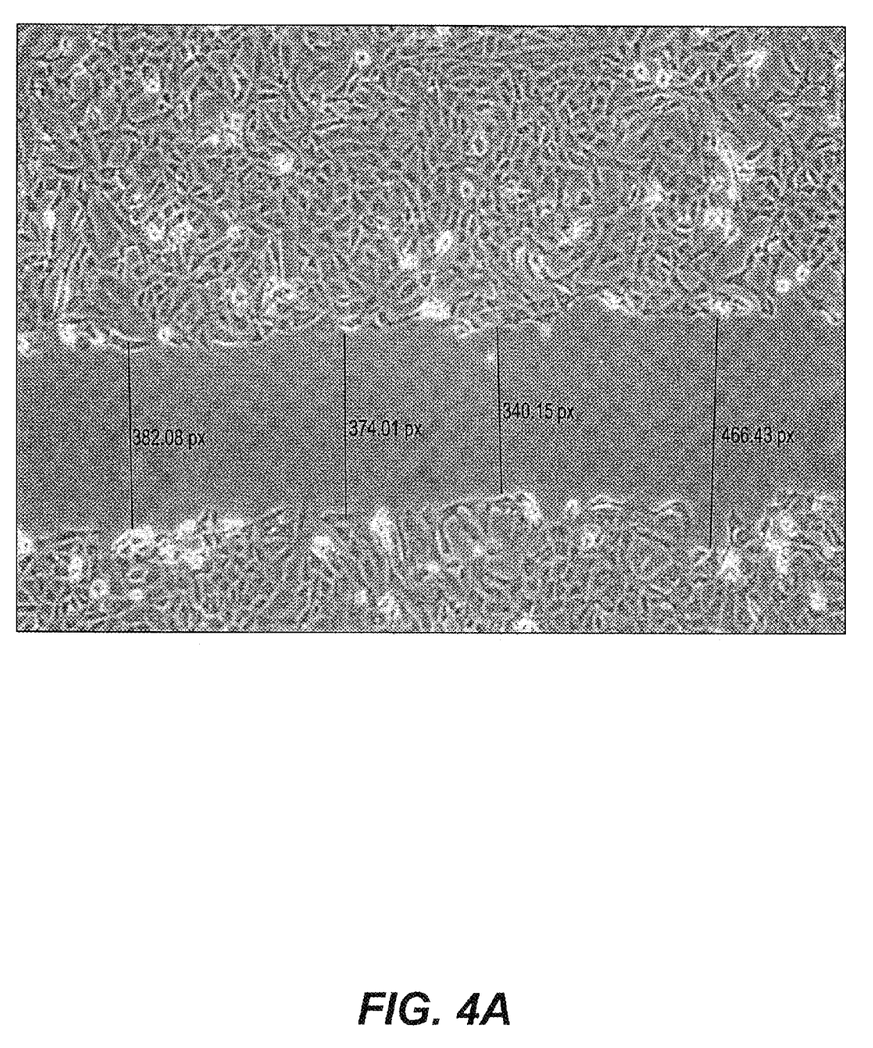
FIGS. 4A and 4B are photomicrographs of a control cell culture (untreated cells) in a scratched wound healing assay at 0-hour and after 24 hours, respectively.
Figure 4B:
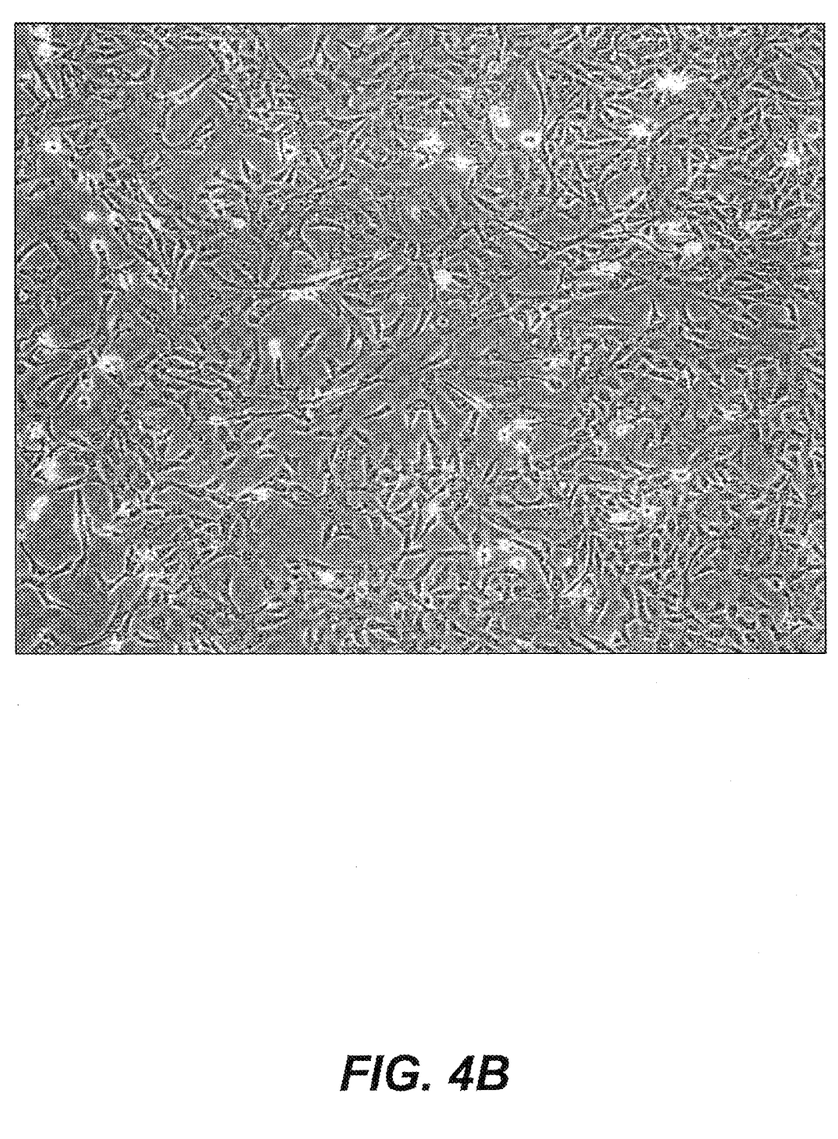
Figure 4C:
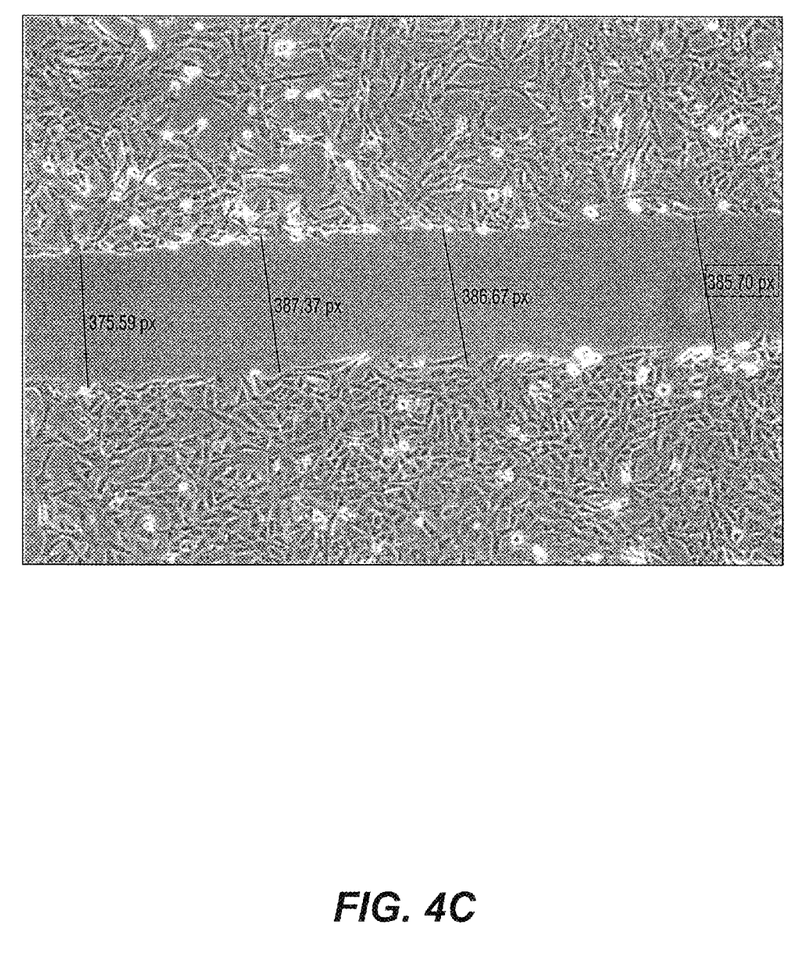
FIGS. 4C and 4D are photomicrographs of a cell culture treated with 10 μg of rutin nanotubes prepared according to the present method in a scratched wound healing assay at 0-hour and after 24 hours, respectively.
Figure 4D:
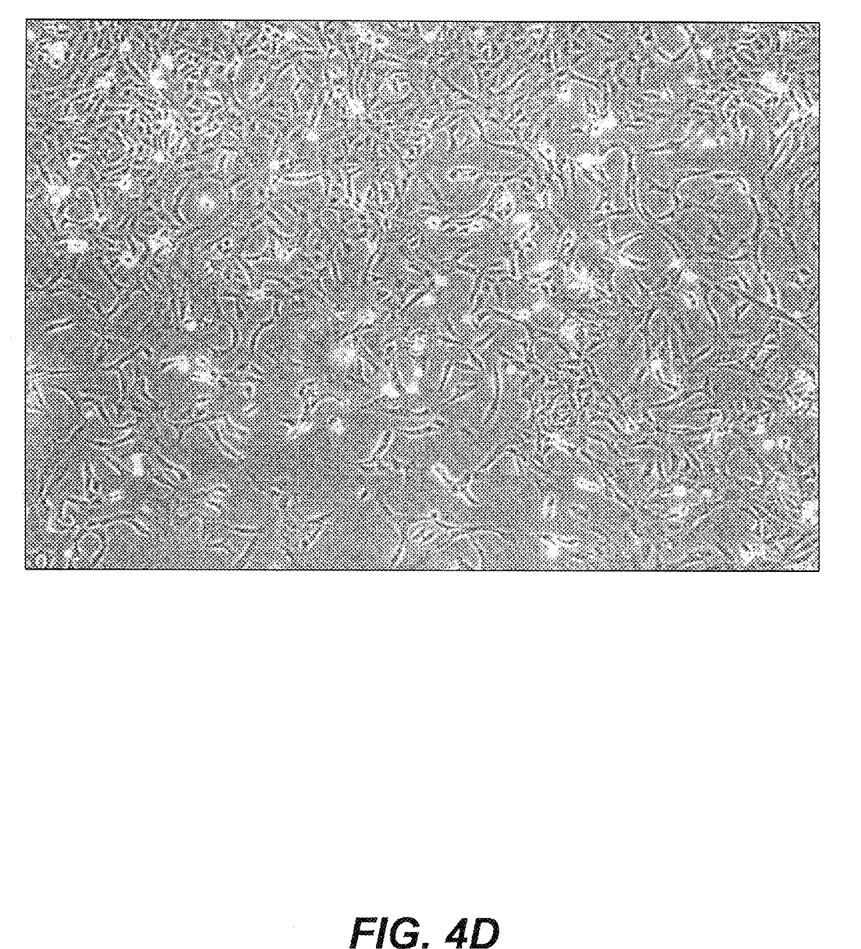
Figure 4E:
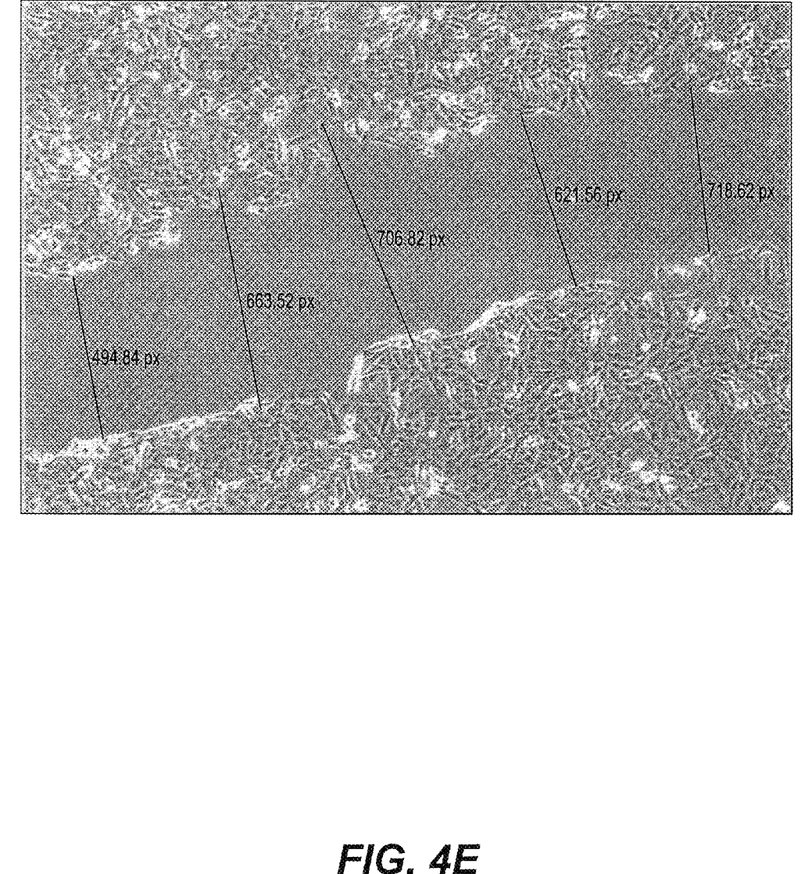
Figure 4F:
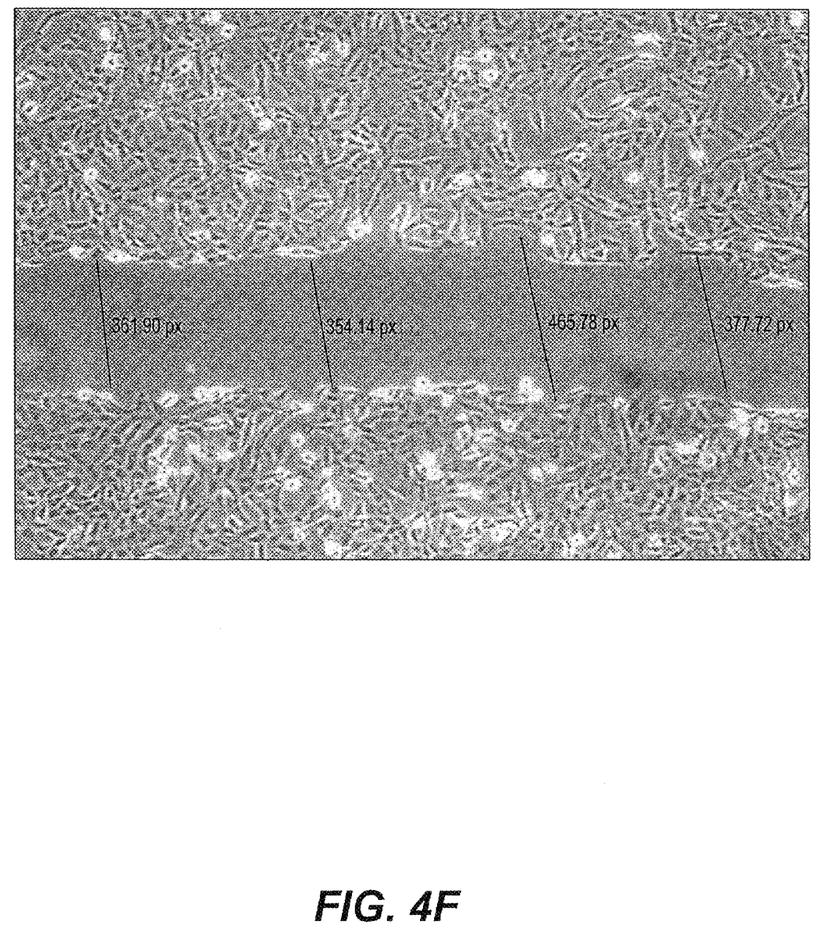
Figure 4G:
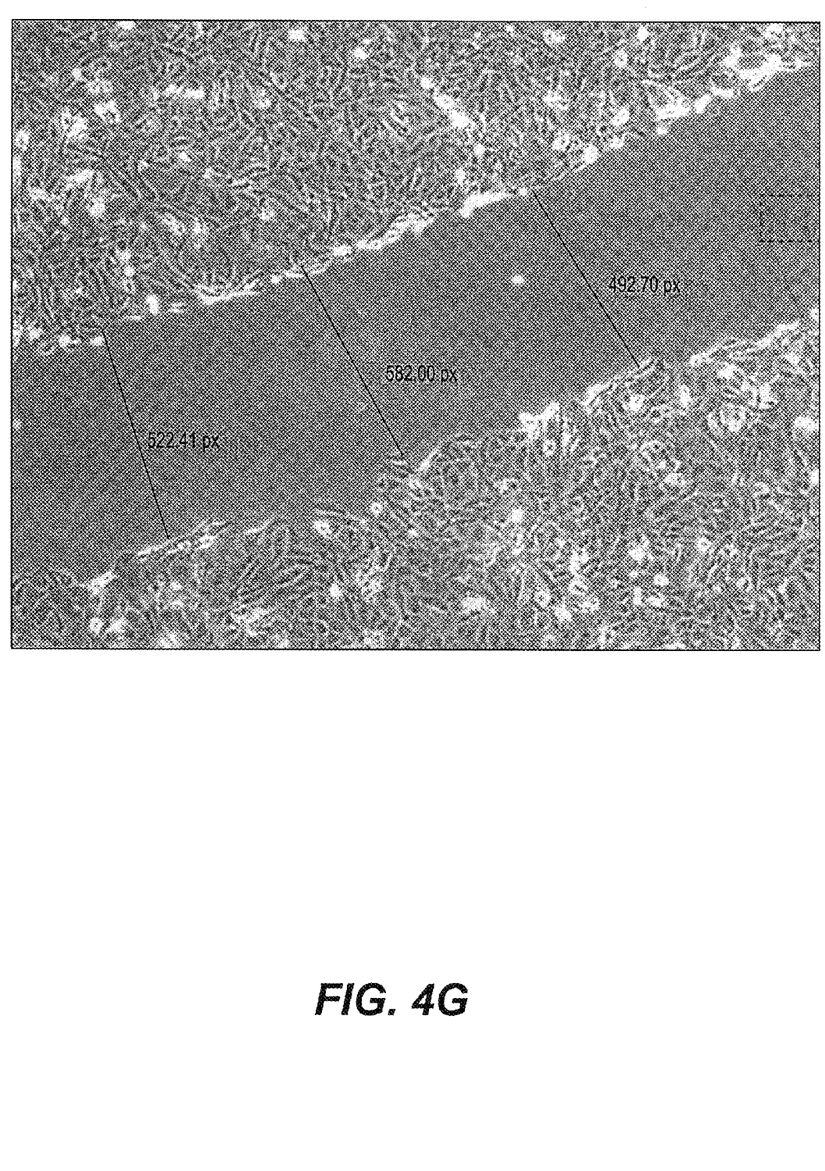
FIGS. 4G and 4H are photomicrographs of a cell culture treated with 40 μg of rutin nanotubes prepared according to the present method in a scratched wound healing assay at 0-hour and after 24 hours, respectively.
Figure 4H:
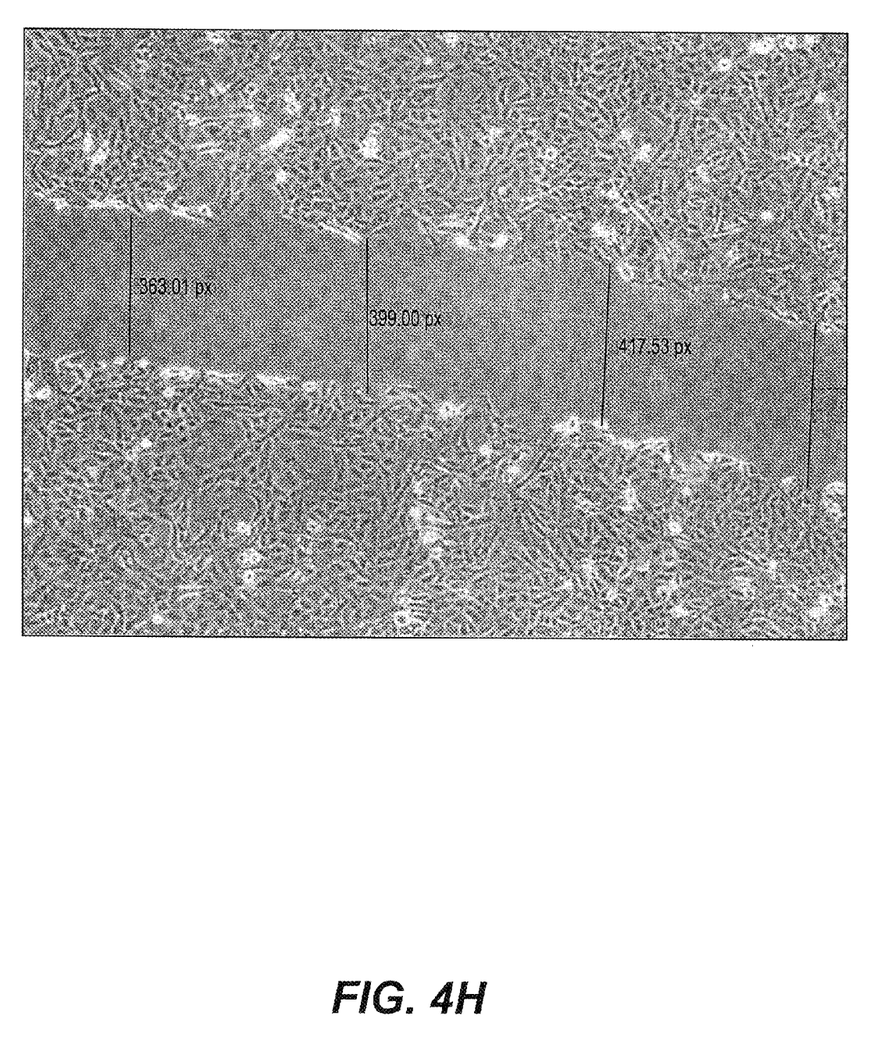

Scratched wound healing assay was performed using the rutin nanoparticles or nanotubes prepared above on Hela cells (a cervical cell line infected with human papilloma virus). A typical image was captured using AmScope image acquisition software, and the distance of scratched area was calculated using the AmScope software. FIGS. 4A-4H display the images of the scratched wound healing assay. FIG. 4A represents the control (non-treatment cells) cells at 0-hour and FIG. 4B after 24-hour (control). FIG. 4C represents cells treated with 10 µg rutin nanotube at 0-hour and FIG. 4D represents the cells treated with 10 µg rutin nanotube after 24-hour. FIG. 4E represents the cells treated with 20 µg rutin nanotube at 0-hour and FIG. 4F represents the cells treated with 20 µg rutin nanotube after 24-hour. FIG. 4G represents the cells treated with 40 µg rutin nanotube at 0-hour and FIG. 4H represents the cells treated with 40 µg rutin nanotube after 24-hour of treatment. FIG. 3A-C shows the effect of different Rutin nanotube concentrations on the relative expression levels of (matrix metalloproteinase-2) MMP2 (FIG. 3A), matrix metalloproteinase-9 (MMP9) (FIG. 3B), and (Tissue inhibitor of metalloproteinases 3) TIMP3 (FIG. 3C), respectively, using real time PCR (polymerase chain reaction) assay.

As is evident from the images from FIGS. 4A-4H and FIGS. 3A-3C, the addition of rutin nanotubes apparently led to a reduction in the number of cells migrating into the scratched area in dose-dependent manner. The MMP2 and MMP9 expression levels were downregulated at 20 µg and 40 µg concentrations compared to the non-treated cell line, whereas TIMP3 expression level was not affected at different concentration levels, compared to non-treated cells. Rutin nanotubes at a dose of 10 µg have no effect on the expression levels of MMP2 and MMP9, compared to non-treated cells, whereas at 20 µg of rutin nanotubes, the expression levels of MMP2 and MMP9 were downregulated by 0.8- and 0.7-fold compared to non-treated cells, respectively. Interestingly, 40 µg doses of rutin nanotubes downregulated the MMP2 and MMP9 expression by 0.18- and 0.22-fold, respectively. In the same manner, a 10 µg dose of rutin nanotubes has no effect on the migration of the cells using the wound healing assay, a 20 µg dose has a mild effect on the migration of Hela cells, but dosages at a concentration of 40 µg of rutin nanotubes completely prevent the migration of the cells, compared to non-treated cells.

The above examples illustrate a novel approach for a simple, low cost, effective, and non-toxic method of synthesis of rutin nanoparticles or nanotubes and the utility of the resulting nanotubes in controlling metastatic activity for a cervical cell line infected with human papilloma virus.

It is to be understood that the present invention is not limited to the embodiments described above, but encompasses any and all embodiments within the scope of the following claims.

We claim:

1. A method for synthesis of rutin nanotubes and nanoparticles, comprising the steps of:
   providing rutin powder;
   mixing the rutin powder with a solvent mixture of methanol, dimethyl sulfoxide, and hydrochloric acid to prepare a rutin solution;
   adding the rutin solution to boiling water dropwise under ultrasonic conditions to form an intermediate solution;
   maintaining the intermediate solution under ultrasonic conditions at room temperature for about 20 minutes;
   continuously stirring the intermediate solution until rutin nanotubes and nanoparticles are formed; and
   isolating the rutin nanotubes and nanoparticles by centrifugation.

2. The method for synthesis of rutin nanotubes and nanoparticles according to claim 1, further comprising drying the rutin nanotubes and nanoparticles to obtain a yellow powder.

3. The method for synthesis of rutin nanotubes and nanoparticles according to claim 1, wherein the step of adding of the rutin solution is completed in under 10 minutes.

4. The method for synthesis of rutin nanotubes and nanoparticles according to claim 1, wherein the ultrasonic conditions include irradiation of ultrasonic waves at a frequency of about 30 to about 60 kHz at a power of about 100 watts.

5. The method for synthesis of rutin nanotubes and nanoparticles according to claim 1, wherein the rutin nanoparticles or nanotubes have a longitudinal dimension of about 10 to 300 nm.

6. The method for synthesis of rutin nanotubes and nanoparticles according to claim 1, wherein the rutin nanotubes and nanoparticles have an average particle size of about 100 to 200 nm.

7. The method for synthesis of rutin nanotubes and nanoparticles according to claim 1, wherein the rutin nanotubes and nanoparticles have spherical, spheroidal, elongated spherical, rod-shaped, or faceted shapes.

8. A method of controlling the metastatic activity of cancer cells, comprising administering an effective amount of the rutin nanotubes and nanoparticles prepared according to claim 1 to a site of metastatic activity in a mammal.

9. The method of controlling the metastatic activity of cancer cells, according to claim 8, wherein the cancer cells are cervical cancer cell line infected by human papillomavirus.

* * * * *